US011589828B2

(12) United States Patent
Ravishankar et al.

(10) Patent No.: US 11,589,828 B2
(45) Date of Patent: Feb. 28, 2023

(54) SYSTEM AND METHODS FOR ELECTROCARDIOGRAM BEAT SIMILARITY ANALYSIS USING DEEP NEURAL NETWORKS

(71) Applicant: GE Precision Healthcare LLC, Milwaukee, WI (US)

(72) Inventors: Hariharan Ravishankar, Bangalore (IN); Rahul Venkataramani, Bangalore (IN)

(73) Assignee: GE Precision Healthcare LLC, Milwaukee, WI (US)

( * ) Notice: Subject to any disclaimer, the term of this patent is extended or adjusted under 35 U.S.C. 154(b) by 466 days.

(21) Appl. No.: 16/733,797

(22) Filed: Jan. 3, 2020

(65) Prior Publication Data

US 2021/0204884 A1 Jul. 8, 2021

(51) Int. Cl.
*G06N 3/084* (2023.01)
*G16H 50/20* (2018.01)
*G16H 40/63* (2018.01)
*G16H 10/60* (2018.01)
*A61B 5/316* (2021.01)
*A61B 5/00* (2006.01)
*G06N 3/04* (2023.01)

(52) U.S. Cl.
CPC ............ *A61B 5/7267* (2013.01); *A61B 5/316* (2021.01); *G06N 3/0454* (2013.01); *G06N 3/084* (2013.01); *G16H 10/60* (2018.01); *G16H 40/63* (2018.01); *G16H 50/20* (2018.01)

(58) Field of Classification Search
CPC ...... A62B 5/7267; G16H 10/60; G16H 50/20; G16H 40/63; A61B 5/316; G06N 3/0454; G06N 3/084

USPC .......................................................... 705/2
See application file for complete search history.

(56) References Cited

U.S. PATENT DOCUMENTS 10,706,329 B2 * 7/2020 Anushiravani ........ G16H 40/67
11,408,978 B2 * 8/2022 Wang .................. A61B 5/0816
(Continued)

OTHER PUBLICATIONS

Hoffer, E. et al., "Deep Metric Learning Using Triplet Network," Cornell University arXiv Website, Available Online at https://arxiv.org/abs/1412.6622, Available as Early as Dec. 20, 2014, 8 pages.
(Continued)

*Primary Examiner* — Michael Tomaszewski
*Assistant Examiner* — Rachael Sojin Stone
(74) *Attorney, Agent, or Firm* — McCoy Russell LLP

(57) ABSTRACT

Methods and systems are provided for automatically determining a phase shift and noise insensitive similarity metric for electrocardiogram (ECG) beats in a Holter monitor recording. In one embodiment, a deep neural network may be trained to map an ECG beat to a phase shift insensitive and noise insensitive feature space embedding using a training data triad, wherein the training data triad may be produced by a method comprising: selecting a first beat and a second beat recorded via one or more Holter monitors, determining a dynamic time warping (DTW) distance between the first beat and the second beat, setting a similarity label for the first beat and the second beat based on the DTW distance, and storing the first beat, the second beat, and the similarity label, in a location of non-transitory memory as an ECG training data triad.

20 Claims, 8 Drawing Sheets

(56) References Cited

U.S. PATENT DOCUMENTS

2013/0046193 A1* 2/2013 Guttag ............... A61B 5/02405
                                                              600/509
2016/0360965 A1* 12/2016 Tran ....................... G16H 50/20
2019/0059763 A1* 2/2019 Shakur ................. A61B 5/7485

OTHER PUBLICATIONS

Koch, G. et al., "Siamese Neural Networks for One-shot Image Recognition," Proceedings of the 32nd International Conference on Machine Learning, Jul. 6, 2015, Lille, France, 8 pages.

Vinyals, O. et al., "Matching Networks for One Shot Learning," Cornell University arXiv Website, Available Online at https://arxiv.org/abs/1606.04080, Available as Early as Jun. 13, 2016, 12 pages.

Snell, J. et al., "Prototypical Networks for Few-shot Learning," Cornell University arXiv Website, Available Online at https://arxiv.org/abs/1703.05175, Available as Early as Mar. 15, 2017, 13 pages.

* cited by examiner

SYSTEM AND METHODS FOR ELECTROCARDIOGRAM BEAT SIMILARITY ANALYSIS USING DEEP NEURAL NETWORKS

TECHNICAL FIELD

Embodiments of the subject matter disclosed herein relate to electrocardiograms, and more particularly, to determining electrocardiogram beat similarity using deep neural networks.

BACKGROUND

A Holter monitor is a long-term electrocardiogram (ECG) measurement device used in ambulatory settings to detect if a subject has irregular/variable heart beats. Holter monitor recordings are typically carried out over a period of 24-48 hours, and comprise a very large number of beats (on the order of one hundred thousand beats). These recordings are retrospectively analyzed by a cardiologist to detect irregularity. This analysis is cumbersome if each beat in the recording is manually analyzed.

Conventional approaches for accelerating interpretation of Holter monitor recordings leverage the redundancy in heart beats to represent the large number of recorded beats using a much smaller set of template beats. Compressing the information contained in a Holter monitor recording in this way enables a cardiologist to form a holistic understanding of a patient's cardiac condition by viewing a handful of distinct beat types (the template beats), along with the relative abundance of each beat type over the period of the Holter monitor recording. This manner of presenting Holter monitor data greatly reduces the time required for a cardiologist to assess the condition of a patient's heart based on an obtained Holter monitor recording, and enables convenient identification of irregular, low abundance beats, without the need for the cardiologist to manually evaluate each of the tens of thousands of beats in the Holter monitor recording.

Representation of a Holter monitor recording using a relatively small set of template beats requires that each of the beats in the Holter monitor recording is classified as belonging to one of the template beat classes/clusters, in a process known as clustering, wherein beats with similar characteristics are grouped together. Each distinct cluster may be represented by an archetypal, template beat, having the average or typical properties of the beats within the cluster. Thus, in order to effectively generate clusters, it is necessary to group ECG beats according to their characteristics, which may rely on determination of a beat similarity metric. Additionally, a beat similarity metric may be useful for classification of ECG beats, longitudinal comparison across multiple Holter monitor recordings, etc. One difficulty in designing a beat similarity metric is that fine grain similarity metrics may be overly sensitive to small variances between otherwise similar beats (e.g., due to noise, amplitude changes/drift, phase differences, etc.) while more course grained similarity metrics may not retain the sensitivity towards clinically relevant changes, important in distinguishing arrhythmic beats from healthy beats. This trade-off between sensitivity and specificity makes designing an appropriate beat similarity metric very challenging, particularly where the beat similarity metric is to be applied to different patient demographics and in different clinical contexts. Most of the current day Holter monitor data clustering approaches use a correlation based distance metric for template generation (e.g., a Euclidean distance). However, correlation based distance metrics are not resilient to small phase shifts and minor amplitude changes, which may result in classification/clustering of beats into incorrect templates/clusters.

Therefore, it is generally desirable to explore techniques for automatically determining a similarity metric for ECG beats, which is sufficiently sensitive to distinguish between healthy/normal beats and unhealthy/arrhythmic beats, while being invariant to phase differences, noise, or other superficial differences between otherwise similar beats.

SUMMARY

The inventors herein have developed systems and methods which may at least partially address the above identified issues. In one embodiment, a deep neural network may be trained to map an ECG beat to a phase shift insensitive and noise insensitive feature space embedding using one or more a training data triads, wherein training data triads may be produced by a method comprising: selecting a first beat and a second beat, determining a dynamic time warping (DTW) distance between the first beat and the second beat, setting a similarity label for the first beat and the second beat based on the DTW distance, and storing the first beat, the second beat, and the similarity label, in a location of non-transitory memory as an ECG training data triad. By determining a similarity label using the phase shift invariant DTW distance, a deep neural network trained using the training data triad described above, may learn a phase shift and noise insensitive mapping from ECG time series data to a feature space, enabling automatic and robust determination of a ECG beat similarity, which may be used to cluster monitor data, perform similar beat search and retrieval, classify ECG beats, distinguish between normal and abnormal beats, and perform longitudinal analysis between monitor recordings of different patients. Further, the above method does not rely on manual labeling of beat similarity, enabling efficient training of deep neural networks on ECG data comprising many hundreds of thousands of beats, which may be impractical for manual labeling by a cardiologist.

The above advantages and other advantages, and features of the present description will be readily apparent from the following Detailed Description when taken alone or in connection with the accompanying drawings. It should be understood that the summary above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

Various aspects of this disclosure may be better understood upon reading the following detailed description and upon reference to the drawings in which.

Figure 1:
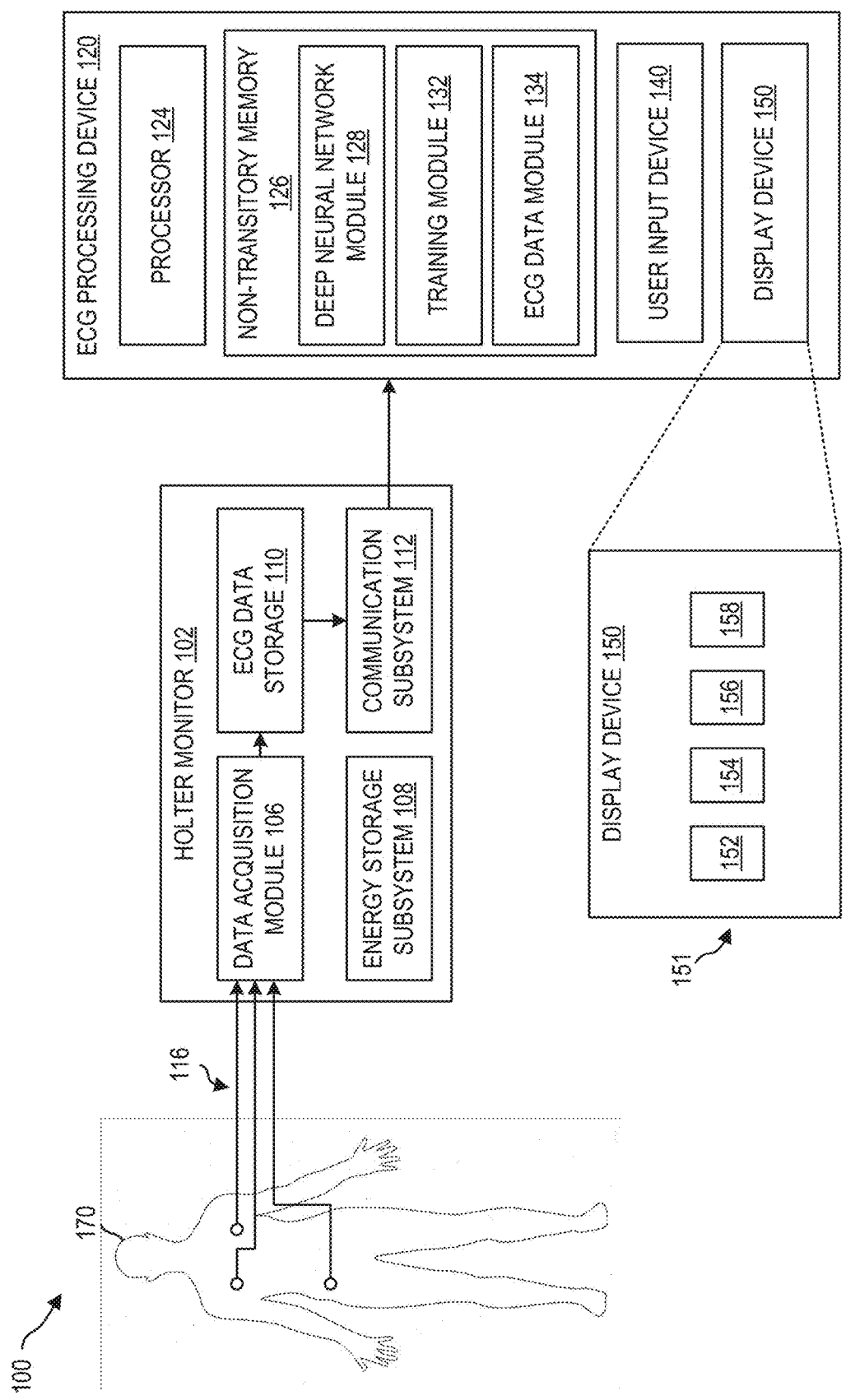
FIG. 1 shows a block diagram of a Holter monitor and an ECG image processing system, according to an exemplary embodiment of the current disclosure.

The drawings illustrate specific aspects of the described systems and methods for mapping ECG beat data to a similarity metric (also referred to herein as a feature space embedding) using one or more deep neural networks. Together with the following description, the drawings demonstrate and explain the structures, methods, and principles described herein. In the drawings, the size of components may be exaggerated or otherwise modified for clarity. Well-known structures, materials, or operations are not shown or described in detail to avoid obscuring aspects of the described components, systems and methods.

DETAILED DESCRIPTION

The following description relates to systems and methods for automatically determining a phase shift and noise insensitive similarity metric for electrocardiogram (ECG) beats in a heart monitor recording, such as a Holter monitor recording, using deep neural networks. The description further discloses systems and methods for training said deep neural network, and for utilizing the similarity metric to cluster a plurality of ECG beats. The clustered beats may be used to produce a template view of the plurality of ECG beats, enabling a clinician to more easily assess a patient's cardiac health, without the need to manually evaluate each of the plurality of beats. Although the current disclosure provides examples in the context of Holter monitor recordings, it will be appreciated that heart beats acquired by other types of monitoring systems, including optical monitoring systems, inertial monitoring systems, etc., may be used in conjunction with the systems and methods described herein.

Dynamic time warping (DTW) distance provides a phase shift, and noise, invariant metric by which similarity of beats recorded via ECG may be evaluated. However, the inventors herein have identified issues with using a DTW distance to compare similarity of ECG beats. In particular, the inventors herein have determined that, owing to the computational complexity of calculating a DTW distance, a DTW distance metric is prohibitively slow for use in clustering the tens or hundreds of thousands of ECG beats in a single Holter monitor recording or other long term ECG recording. Further, a DTW distance metric lacks flexibility, and is unable to be adapted to particular use cases, particular patient populations, particular physician preferences etc.

The inventors herein provide systems and methods which may at least partially address the above identified issues. In one example, by using DTW distance to determine beat similarity labels during generation of a training dataset, a deep neural network may be trained to map ECG beats separated by less than a threshold DTW distance to similar/proximal points in a feature space, and conversely, to map ECG beats separated by greater than the threshold DTW distance to points in the feature space separated by greater than a pre-determined Euclidean distance (herein referred to as a margin). Thus, proximal points in the feature space may correspond to similar ECG beats, invariant of phase shifts or noise within the corresponding ECG data. Once trained, the deep neural network may use the learned mapping between the ECG data space and the feature space to compare ECG beats using corresponding feature space embeddings, without performing calculation of DTW distance metrics, thereby reducing a computational cost and increasing a speed of ECG beat similarity analysis. Further, as deep neural networks may be trained in a process known as on-line learning, the initially learned mapping between the ECG data space and the feature space may be further refined during implementation in particular use cases (e.g., for particular patient demographics, hospitals, regions, case histories, etc.) to meet clinicians' expectations.

In one embodiment, ECG data acquired by a monitor, such as Holter monitor 102 of FIG. 1, may be transferred to an ECG processing device 120. While a Holter monitor may be one option, monitors may be used that may be optical, electrical, and/or combinations thereof. Further, other approaches may also be used to generate ECG beats, such as pressure sensing, flow sensing, and/or combinations thereof. The ECG processing device 120 may perform one or more of the steps of method 300 of FIG. 3, to automatically generate a training dataset comprising a plurality of training data triads using the Holter monitor acquired ECG data. Each training data triad may include a pair of ECG beats, and a dynamic time warping (DTW) based similarity label, indicating if the pair of beats are within a threshold DTW distance of each other. Briefly, DTW distance is a phase shift and noise invariant similarity metric for time series data. For example, a DTW distance between a first pair of beats 602, and a DTW distance between a second pair of beats 604 (shown in FIG. 6), may be similar, whereas a Euclidean distance between the first pair of beats 602 may be significantly smaller than a Euclidean distance between the second pair of beats 604, despite the fact that both the first pair of beats 602 and the second pair of beats 604 appear similar to a human observer. In other words, DTW distance more closely matches human intuition regarding similarity in time series data, whereas Euclidean distance metrics may be particularly sensitive to phase shifts and/or other types of time warping noise. Therefore, by determining the similarity label using a DTW distance threshold, a deep neural network trained using the training data triads may learn to map the ECG beat data to a phase shift and noise invariant feature space embedding, therefore providing benefits of a DTW distance metric, at a fraction of the time, and without the computational cost.

Figure 2:
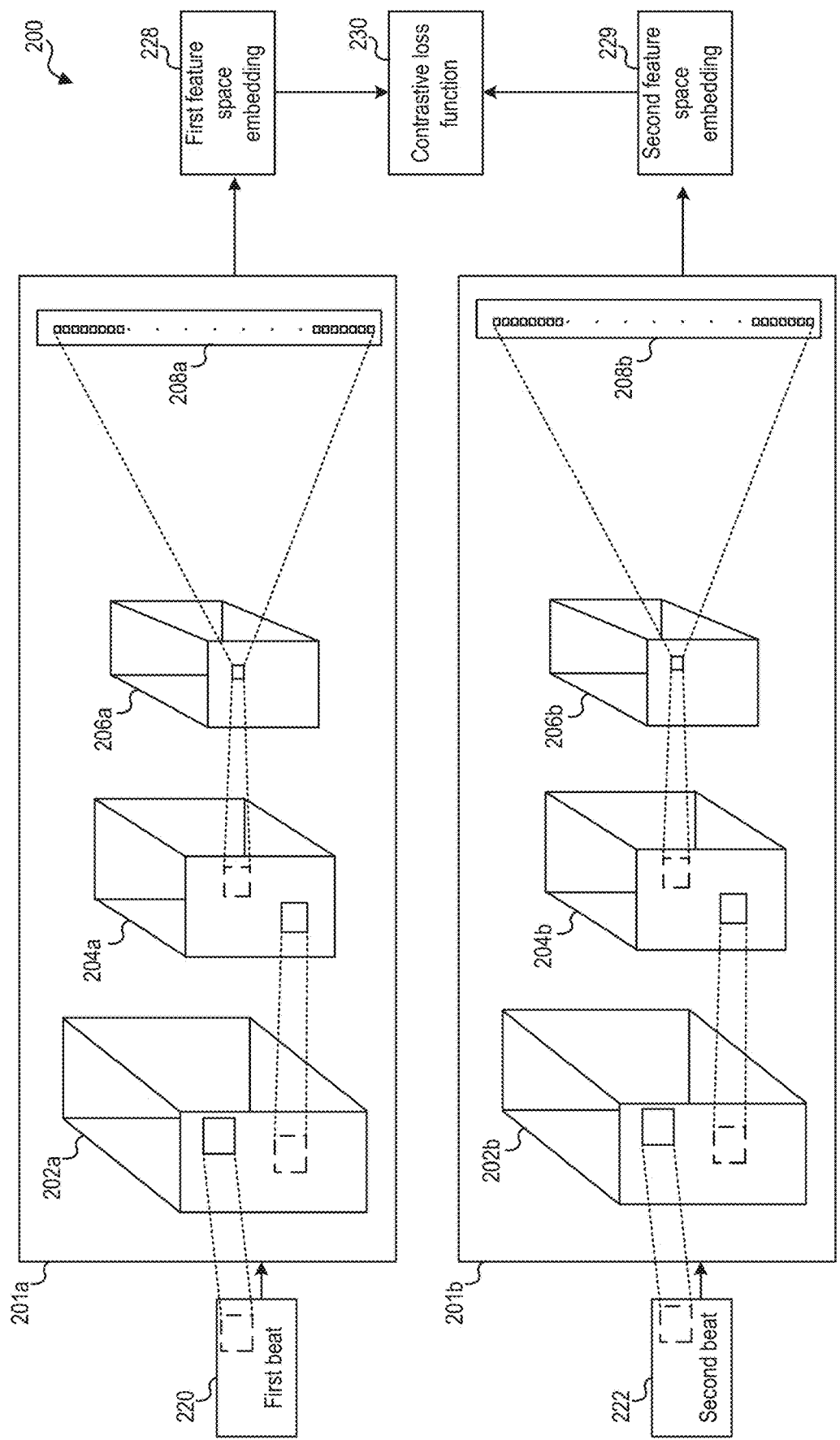
FIG. 2 shows a block diagram of a siamese neural network training architecture, according to an exemplary embodiment of the current disclosure.
Figure 4:
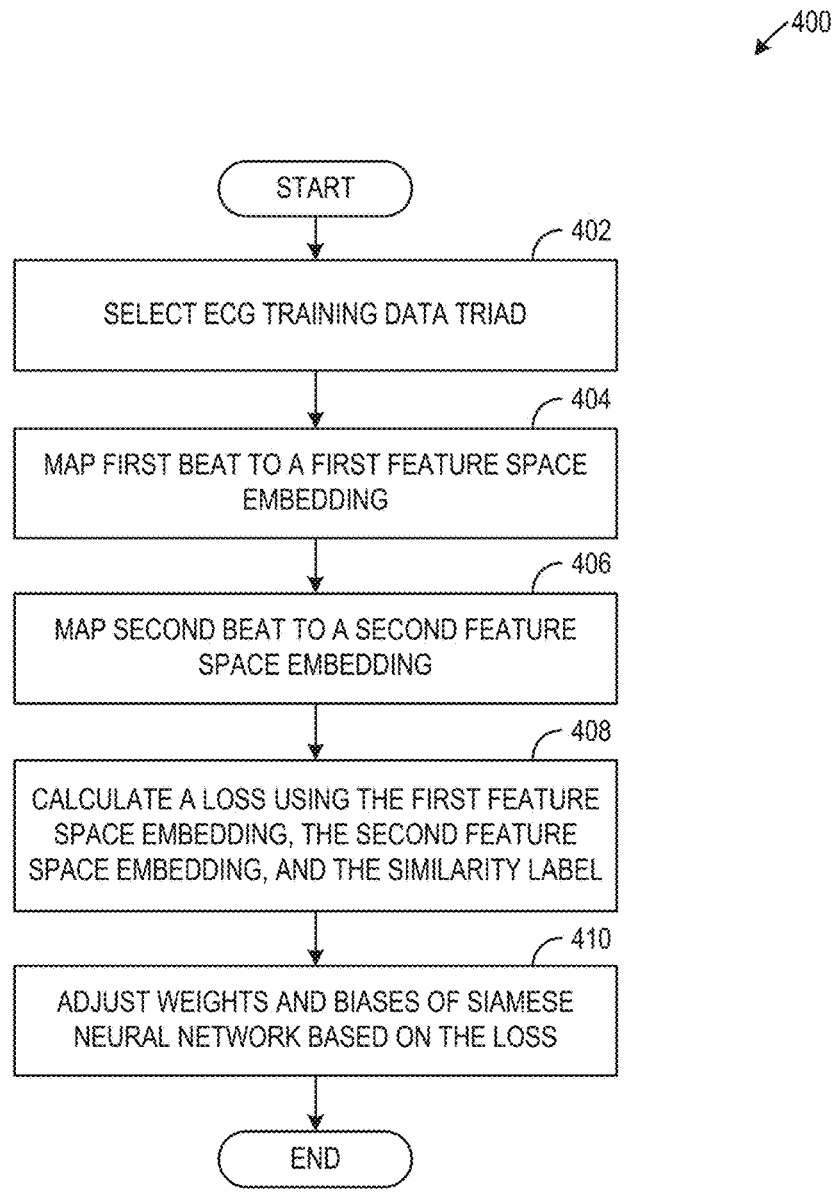
FIG. 4 is a flowchart illustrating an exemplary method for training the deep neural network using the training data triads, according to an exemplary embodiment of the current disclosure.
Figure 7:
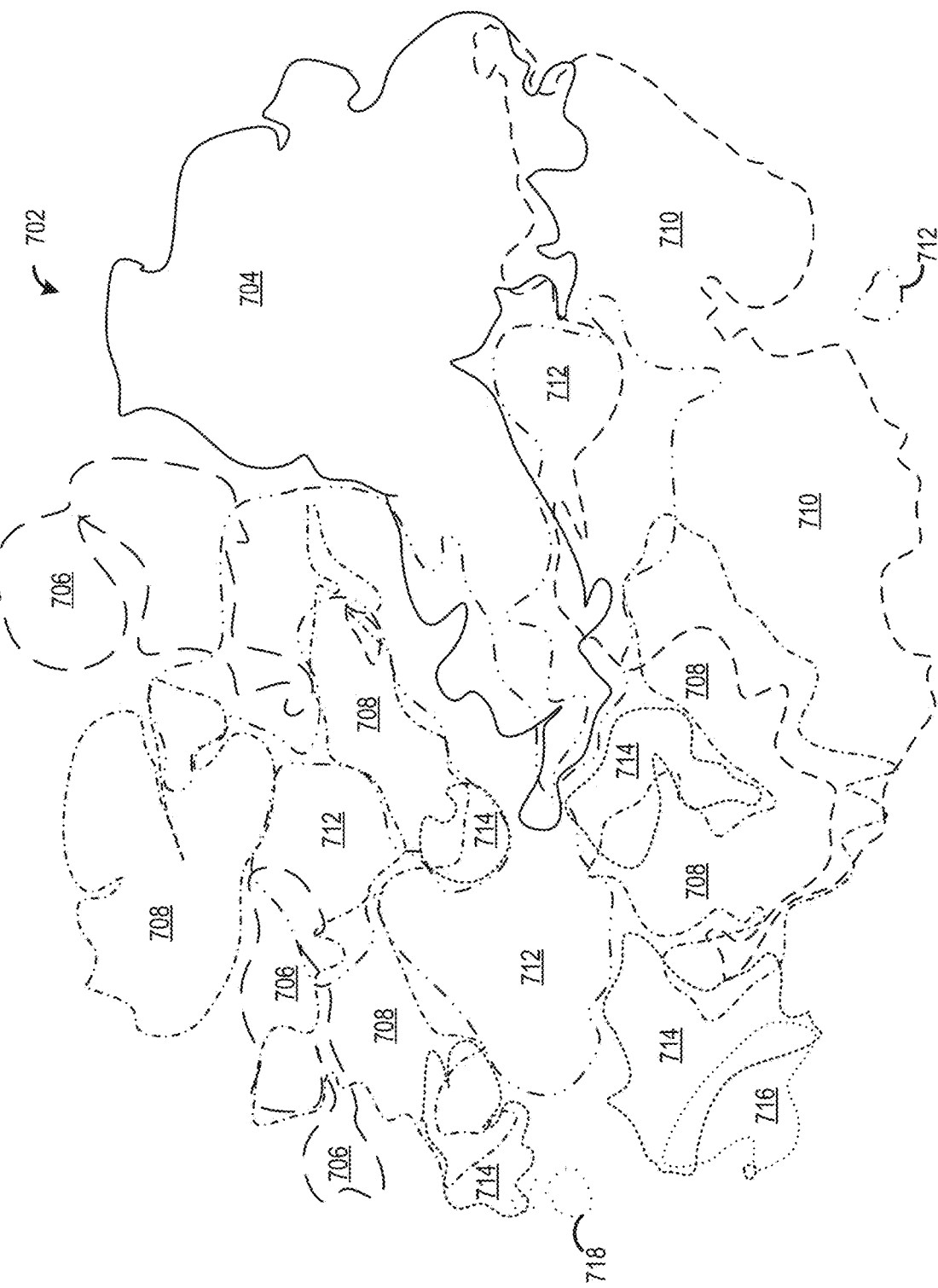
FIG. 7 shows an example of clusters produced in a feature space for a plurality of beats of a Holter monitor recording, according to an exemplary embodiment of the current disclosure.

The training data triads may be used to train a deep neural network, such as first subnetwork 201a and/or second subnetwork 201b, shown in FIG. 2, according to one or more of the steps of method 400, shown in FIG. 4. Once trained, the deep neural network may be implemented according to one or more steps of method 500, shown in FIG. 5, to map a plurality of ECG beats to a plurality of feature space embeddings, and cluster the plurality of ECG beats based on the plurality of feature space embeddings. FIG. 7 shows one example of a plurality feature space embeddings of a plurality of ECG beats, which may be produced according to one or more of the steps of method 500. The clustered beats may be used to produce a template view of a long term cardiac recording, such as the template view 802 shown in FIG. 8.

Referring to FIG. 1, one embodiment of a long term ECG monitoring system 100 is shown. Long term ECG monitoring system 100 comprises a Holter monitor 102, and an ECG processing device 120 communicably coupled thereto. Holter monitor 102 is one embodiment of a portable ECG monitoring device, which may be worn/carried by a patient for a clinician prescribed duration of time (e.g., 24-48 hours). The Holter monitor 102 is configured to measure and store a recording of the electrical activity of a patient 170's heart, over the prescribed duration of time. For an average heart rate of 70 beats per minute, a 24 hour Holter monitor recording may include 100,800 recorded beats, wherein each beat may be recorded in multiple channels, thereby multiplying the number or recorded beats by the number of channels.

The ECG data recorded by Holter monitor 102 comprises time series data, wherein an electrical potential (voltage) between two or more electrodes in electrical contact with patient 170's skin (such as electrodes 116) is recorded as a function of time. Although FIG. 1 includes Holter monitor 102, it will be appreciated that other means of recording heart activity through time may be used, such as by recording periodic movement of an inertial sensor placed on a patient's body, or by monitoring changes in appearance of a patient in time using an optical sensor.

The ECG data acquired by Holter monitor 102 may be transferred to an ECG processing device 120, for further processing before being evaluated by a cardiologist. The cardiologist may evaluate the ECG data acquired by the Holter monitor 102 for signs of arrhythmia or other cardiac disorder. In one embodiment, to facilitate cardiologist evaluation of the ECG data acquired by the Holter monitor 102, ECG processing device 120 may employ a trained deep neural network to map the plurality of beats in the ECG data to a corresponding plurality of feature space embeddings, according to one or more of the steps of method 500, described in more detail below, with reference to FIG. 5. The feature space embeddings may be used to cluster the ECG beats, wherein related/similar beats may be grouped together, enabling a more compact representation (e.g., a template view such as in FIG. 8) of the ECG data to be presented to the cardiologist.

Holter monitor 102 comprises a plurality of electrodes 116, which include a right arm electrode, a left arm electrode, and leg electrode, which are attached to patient 170 via adhesive pads and/or electrically conductive gel, enabling Holter monitor 102 to measure ECG data by determining a difference in electrical potential between two or more electrodes of electrodes 116. In the embodiment shown by FIG. 1, electrodes 116 are configured to measure a three lead ECG, wherein electrical potential is measured along three distinct axes passing through the heart of patient 170. Although the embodiment of Holter monitor 102 shown in FIG. 1 comprises three electrodes and is configured to measure a three lead ECG, it will be appreciated that the current disclosure provides for Holter monitors comprising more or less than three electrodes, and/or Holter monitors configured to measure more or less than three leads. The current disclosure also provides for electrode placement other than that described above with reference to electrodes 116. In some embodiments, a Holter monitor comprising four limb electrodes, and no chest electrodes, may record six limb leads, but may not record six chest leads. In some embodiments, a Holter monitor comprising the four limb electrodes, and two chest electrodes (V1 and V5) may record six limb leads, and two of the six chest leads (V1 and V5), but may not measure the other four chest leads (V2, V3, V4, and V6). In some embodiments, a Holter monitor comprising the four limb electrodes, and two chest electrodes (V2 and V5) may record the six limb leads, and two of the six chest leads (V2 and V5), but may not measure the other four chest leads (V1, V3, V4, and V6).

Electrodes 116 may be electrically coupled to data acquisition module 106 of Holter monitor 102. Data acquisition module 106 is configured to measure electrical potential differences between two or more of electrodes 116 as a function of time, and record this data in ECG data storage 110. In some embodiments, data acquisition module 106 may be configured to receive analog electrical signals from electrodes 116, amplify and/or filter the analog signals, and convert the analog signals to digital signals, before storing the digital signals as a function of time in ECG data storage 110. In another embodiment, data acquisition module 106 may convert the analog electrical signals from electrodes 116 to a digital signal, and may amplify and/or filter the digital signal before storing the digital signal as a function of time in ECG data storage 110. In some embodiments, data acquisition module 106 may be configured to differential amplify signals from each lead, thereby adjusting for differences in signal intensity.

Data acquisition module 106 is communicably coupled with ECG data storage 110, and may write ECG data acquired from patient 170 to ECG data storage 110 for storage. ECG data storage 110 may comprise non-transitory memory, wherein the ECG data acquired by data acquisition module 106 may be stored. ECG data stored in ECG data storage 110 may comprise time series data, wherein an amplitude of the electrical potential difference between two or more electrodes 170 is recorded at regular intervals in time, wherein each recorded electrical potential difference is time stamped with the time of acquisition, thereby creating time series data. A storage capacity of ECG data storage 110 may be selected such that an expected number of beats from one or more Holter monitor recordings may be stored thereon. In some embodiments, ECG data storage 110 may comprise a removable component, enabling a user to physically remove ECG data storage 110 from Holter monitor 102. In some embodiments, ECG data storage 110 may comprise a memory card, a flash drive, or a removable hard drive. In some embodiments, ECG data storage 110 may be integrated into Holter monitor 102, and may include a solid state drive (SSD), hard disk drive (HDD).

Holter monitor 102 further comprises energy storage subsystem 108, wherein electrical energy may be stored, enabling Holter monitor 102 to operate while attached to a patient for hours or days without requiring the patient to plug the Holter monitor into an outlet. In some embodiments, energy storage subsystem 108 comprises a rechargeable battery.

In some embodiments, Holter monitor 102 and ECG processing device 120 may be reversibly communicably coupled by communication subsystem 112. In one embodiment, communication subsystem 112 may comprise a wireless or wired connection configured to transfer ECG data from ECG data storage 110 of Holter monitor 102 to ECG processing device 120. In some embodiments, communication subsystem 112 may enable Holter monitor 102 and ECG processing device to be in substantially continuous communicative coupling, via a wireless network, enabling ECG processing device 120 to receive substantially real time ECG data from Holter monitor 102. Communication subsystem 112 may include wired and/or wireless communication devices compatible with one or more different communication protocols. As non-limiting examples, communication subsystem 112 may be configured to transfer ECG data from ECG data storage 110 to ECG processing device 120 via a wireless telephone network, a wireless local area network, a wired local area network, a wireless wide area network, a wired wide area network, etc. In some embodiments, communication subsystem 112 may allow Holter monitor 102 to send and/or receive data to and/or from other devices via a network such as the public Internet. For example, communication subsystem 112 may communicatively couple Holter monitor 102 with consumer ECG processing device 120 via a network, such as the public Internet.

ECG data acquired by Holter monitor 102 may be transferred to ECG processing device 120 for long term storage, processing (e.g., signal filtering, normalization, noise suppression, etc.), display, and diagnosis. In one embodiment, ECG processing device 120 may comprise a deep neural network, such as a siamese neural network, trained to map ECG beat data to a phase shift and noise invariant, feature space embedding by executing instructions to perform one or more of the steps of method 400, using training data produced according to one or more of the steps of method 300. ECG processing device 120 may further comprise instructions, that when executed, cause processor 124 to perform one or more of the steps of method 500, to cluster feature space embeddings, and to produce a template view of the ECG data for display to a cardiologist based on the clustered feature space embeddings. In some embodiments, ECG processing device 120 may comprise instructions for generating a training dataset, comprising a plurality of training data triads, using the ECG data acquired by Holter monitor 102, by executing one or more of the steps of method 300. The ECG processing device 120 may further include instructions, that when executed, cause ECG processing device 120 to perform one or more of the steps of method 400, to train a deep neural network to learn a mapping from an ECG data space to a phase shift and noise invariant feature space.

ECG processing device 120 includes a processor 124 configured to execute machine readable instructions stored in non-transitory memory 126. Processor 124 may be single core or multi-core, and the programs executed thereon may be configured for parallel or distributed processing. In some embodiments, the processor 124 may optionally include individual components that are distributed throughout two or more devices, which may be remotely located and/or configured for coordinated processing. In some embodiments, one or more aspects of the processor 124 may be virtualized and executed by remotely-accessible networked computing devices configured in a cloud computing configuration.

Non-transitory memory 126 may store deep neural network module 128, training module 132, and ECG data module 134. Deep neural network module 128 may include one or more trained and/or untrained deep neural networks, such as siamese neural networks, comprising a plurality of weights and biases, activation functions, loss functions, and instructions for implementing the one or more deep neural networks to receive ECG beat data and map the ECG beat data to a feature space embedding corresponding to a phase shift and noise invariant representation of the ECG beat. In one embodiment, deep neural network module 128 may include machine executable instructions for implementing a neural network, such as a siamese neural, according to one or more steps of method 500, shown in FIG. 5, to map ECG a plurality of ECG beat data to a plurality of corresponding feature space embeddings. The plurality of feature space embeddings may be used to produce a plurality of clusters, according to a clustering algorithm, wherein each cluster may correspond to a distinct beat type, thereby enabling a more compact/compressed view of a Holter monitor recording to be displayed to a clinician for diagnosis.

Deep neural network module 128 may include trained and/or untrained neural networks and may further include various deep neural network metadata pertaining to the trained and/or untrained networks. In some embodiments, the deep neural network metadata may include an indication of the training data used to train a trained deep neural network, a training method employed to train a trained deep neural network, an accuracy/validation score of a trained deep neural network, and a type of use-case/protocol for which the trained deep neural network may be applied.

Non-transitory memory 126 further includes training module 132, which comprises machine executable instructions for training one or more of the deep neural networks stored in deep neural network module 128. In one embodiment, the training module 132 may include gradient descent algorithms, loss functions, and rules for generating and/or selecting training data for use in training a particular deep neural network. In one embodiment, training module 132 may include instructions, that when executed by processor 124, cause ECG processing device 120 to access ECG data stored in ECG data module 134 and generate ECG training data triads from the ECG data stored therein according to one or more steps of method 300, shown in FIG. 3. Training module 132 may further include instructions, that when executed, cause ECG processor 120 to train a deep neural network, by executing one or more of the steps of methods 400, using the training data triads, discussed in more detail with reference to FIGS. 3 and 4. In some embodiments, the training module 134 is not disposed at the ECG processing device 120, but is disposed remotely, and is communicably coupled with ECG processing device 120.

Non-transitory memory 126 further includes ECG data module 134, which may include Holter monitor data collected from one or more patients, comprising Holter monitor recordings, wherein the Holter monitor recordings comprise a plurality of ECG beats, acquired by one or more Holter monitors, such as Holter monitor 102. In some embodiments, ECG data module 134 may receive ECG data from Holter monitor 102, and may store the ECG data received therefrom. In some embodiments, ECG processing device 120 may receive ECG data from a plurality of data sources, including one or more network devices. ECG data stored within ECG data module 134 may be organized according to one or more organizational schemes, or configured into one or more data structures known in the art of data storage. In some embodiments, ECG data may be stored in ECG data module 134 by indexing the ECG data according to patient, acquisition time, originating Holter monitor ID, etc. In some embodiments, ECG beats originating from a single Holter monitor recording may be grouped together, facilitating analysis of a patient's Holter monitor data.

ECG data module 134 may further comprise ECG training data triads, produced by training module 132, according to one or more of the steps of method 300. Further, the training data triads stored therein may be grouped into distinct training datasets. Each training data triad may comprise a pair of ECG beats, along with a similarity label. In some embodiments, the similarity label comprises a binary label, indicating if the pair of ECG beats is similar, or dissimilar.

In some embodiments, the non-transitory memory 106 may include components disposed at two or more devices, which may be remotely located and/or configured for coordinated processing. In some embodiments, one or more aspects of the non-transitory memory 106 may include remotely-accessible networked storage devices configured in a cloud computing configuration.

ECG processing device 120 further includes user input device 140. User input device 140 may comprise one or more of a touchscreen, a keyboard, a mouse, a trackpad, a motion sensing camera, or other device configured to enable a user to inter, interact with, and/or manipulate, data within ECG processing system 102. In some embodiments, a user may specify a dynamic time warping (DTW) distance threshold, using user input device 140, wherein the DTW distance threshold may be used to automatically generated ECG training data triads, such as at operation 314 of method 300.

Display device 150 may include one or more display devices utilizing virtually any type of technology. In some embodiments, display device 150 may comprise a computer monitor, and may display unprocessed and/or processed ECG data. Display device 150 may be combined with processor 124, non-transitory memory 126, and/or user input device 140 in a shared enclosure, or may be peripheral display devices and may comprise a monitor, touchscreen, projector, or other display device known in the art, which may enable a user to view ECG data and/or interact with various data stored in non-transitory memory 106. In some embodiments, clustered ECG data (such as clustered ECG data 702, shown in FIG. 7), and/or a template view of ECG data, such as template view 802 shown in FIG. 8, of a Holter monitor recording may be displayed to a user, via display device 150. In one embodiment, a template view of a Holter monitor recording, may be displayed via display device 150. A magnified view 151 of the display device 150 is indicated in FIG. 1, showing representative beats 152, 154, 156, and 158 from a clustered ECG data. In some embodiments, display device 150 may display a template view, such as template view 802 shown in FIG. 8, of the plurality of recorded beats.

It should be understood that long term ECG monitoring system 100, shown in FIG. 1, is for illustration, not for limitation. Another appropriate long term ECG monitoring system may include more, fewer, or different components.

Turning to FIG. 2, a block diagram of a training architecture 200, for training a deep neural networks 201a and/or 201b, is shown. Training architecture 200 may be implemented by one or more of the systems described herein, such as ECG processing system 120, executing machine readable instructions stored in non-transitory memory. Training architecture 200 comprises a pair of identical "twin" or siamese, subnetworks, first subnetwork 201a, and second subnetwork 201b. First subnetwork 201a and second subnetwork 201b have the same number, type and arrangement of layers, as well as the same parameters within each layer. Thus, although discussed herein as comprising distinct subnetworks, it will be appreciated that training architecture 200 comprises a single set of deep neural network parameters, representing both first subnetwork 201a and second subnetwork 201b. During clustering of Holter monitor data, e.g., at operation 506 of method 500, a single, trained subnetwork may be used, as both subnetworks 201a and 201b comprise identical parameters in an identical configuration, and upon completion of training, both subnetworks 201a and 201b may comprise a same set of learned weights/parameters. Subnetwork 201a and subnetwork 201b may be used to determine pairwise similarity of ECG beats, and in such cases, both subnetworks may be employed in parallel to map the pair of ECG beats to a pair of feature space embeddings, wherein the pairwise similarity of the ECG beats may be assessed based on a feature space distance between the pair of feature space embeddings (that is, between a pair of points in feature space uniquely defined by the pair of feature space embeddings). In some embodiments, more than two subnetworks may be implemented in parallel, such as three or more subnetworks, to map in parallel a plurality of beats to a plurality of phase shift and noise invariant feature space embeddings (e.g., to map three or more ECG beats in parallel to three or more corresponding feature space embeddings).

Training architecture 200 is configured to receive a pair of ECG beats, such as first beat 220 and second beat 222, at first subnetwork 201a, and second subnetwork 201b, respectively, and to map the pair of beats to a corresponding pair of feature space embeddings, such as first feature space embedding 228, and second feature space embedding 229. In some embodiments, first beat 220 and/or second beat 222 comprise two-dimensional (2D) time series data, wherein the electrical potential through time, measured along an axis through a heart of a patient via a Holter monitor, may be represented as a 2D matrix of values, wherein a first dimension may correspond to time, and a second dimension may correspond to electrical potential difference between two or more Holter monitor electrodes. In some embodiments 2D ECG data may comprise an image file, wherein the ECG time series data may be represented by pixels of a predetermined color. In some embodiments, ECG data may comprise one-dimensional (1D) data, representing an ECG beat as a sequence (vector) of values (e.g., voltage values), wherein each element of the sequence (e.g., each row of the vector) corresponds to a distinct voltage, measured at a distinct time point. Therefore, it will be appreciated that the convolutional layers, and convolutional filters, discussed herein, may comprise 2D convolutional filters, or 1D convolutional filters, wherein 2D convolutional filters may be used for 2D ECG data, and wherein 1D convolutional filters may be used for 1D ECG data.

First subnetwork 201a maps first beat 220 to first feature space embedding 228 by performing a series of linear and non-linear transformations on the ECG data within first beat 220, according to the learned parameters of first subnetwork 201a. In particular, first subnetwork 201a receives first beat 220, which may comprise 1D or 2D ECG data, and maps first beat 220 to first feature map 202a, by passing first beat 220 through one or more convolutional filters. Each convolutional filter may comprise a plurality of learned weights arranged into a fixed pattern, this fixed pattern of weights may be referred to as a feature. Each convolutional filter may be "passed" over each subregion of the input data, based on a pre-determined stride and receptive field of the filter, and each subregion of the input may be mapped to a corresponding sub-region of an output feature map based on the degree of match between the subregion and the filter. In other words, features present in first beat 220, which match one or more of the convolutional filters, may be extracted and mapped to feature map 202a. Said another way, feature map 202a comprises a map of the spatial distribution of features identified by one or more convolutional filters in first beat 220.

Further, output of one or more convolutional filters may be fed to an activation function, and/or pooled, prior to being output to a subregion of a subsequent feature map. Pooling provides dimensionality reduction in the input data, which may provide a greater degree of feature identification in exchange for spatial resolution, whereas activation functions provide non-linearity to the mapping of the subnetworks 201a and 201b, and enable first subnetwork 201a to approximate non-linear functions. In some embodiments, activation functions may comprise a rectified linear unit (ReLU), or other activation functions known in the art of machine learning. In some embodiments, pooling may comprise max pooling operations, wherein a maximum value in a subregion of an input is passed to a corresponding subregion of an output feature map, while other values in the subregion are not passed. In other embodiments, pooling may comprise average pooling, wherein an average value for a subregion of an input is calculated, and propagated to a corresponding subregion of a subsequent feature map.

First feature map 202a may likewise be passed through one or more convolutional layers, pooling layers, and activation functions, to produce second feature map 204a, which in turn may be passed through one or more convolutional layers, pooling layers, and activation functions to produce third feature map 206a. Third feature map 206a may be mapped via a dense layer/fully connected layer to first output layer 208a. In a dense layer, every node/neuron of an input layer/feature map is connected to every node/neuron of a subsequent layer. In some embodiments, first output layer 208a comprises an n-dimensional vector. First output layer 208a may be mapped to first feature space embedding 228, comprising an n-dimensional vector, wherein each row comprises a value corresponding to a coordinate in an n-dimensional feature space. Said another way, first feature space embedding 228 may comprise a vector representation of a point in a feature space (referred to herein as a feature space embedding), corresponding to first beat 220, wherein each row of first feature space embedding 228 corresponds to a coordinate in the n-dimensional feature space.

Similarly, second subnetwork 201b maps second beat 222 to fourth feature map 202b, via one or more convolutional filters, pooling operations, and activation functions, as described above with reference to first subnetwork 201a. Fourth feature map 202b is likewise passed through one or more convolutional filters, pooling layers, and activation functions, to produce fifth feature map 204b, which is in turn passed through one or more one or more convolutional filters, pooling operations and activation functions to produce sixth feature map 206b. Sixth feature map 206b may be mapped via a dense layer/fully connected layer to second output layer 208b. In some embodiments, second output layer 208b comprises an n-dimensional vector. Second output layer 208b may be mapped to second feature space embedding 229, comprising an n-dimensional vector, wherein each row comprises a value corresponding to a coordinate in an n-dimensional feature space. Said another way, second feature space embedding 229 may comprise a vector representation of a point in a feature space (referred to herein as a feature space embedding), corresponding to second beat 222, wherein each row of second feature space embedding 229 corresponds to a coordinate in the n-dimensional feature space.

Both the first feature space embedding 228 and the second feature space embedding 229, may be received by a contrastive loss function 230, wherein a contrastive loss may be calculated based on the first feature space embedding 228 and the second feature space embedding 229, along with a similarity label, as is discussed in more detail with reference to operation 408, discussed in the description of FIG. 4, below.

While the present example illustrates a siamese network training architecture, it will be appreciated that other similar or derived training architectures, such as a triplet network training architecture, matching network architectures, relational network architectures, prototypical network architectures, or combinations thereof, may be used, without departing from the scope of the current disclosure.

Figure 3:
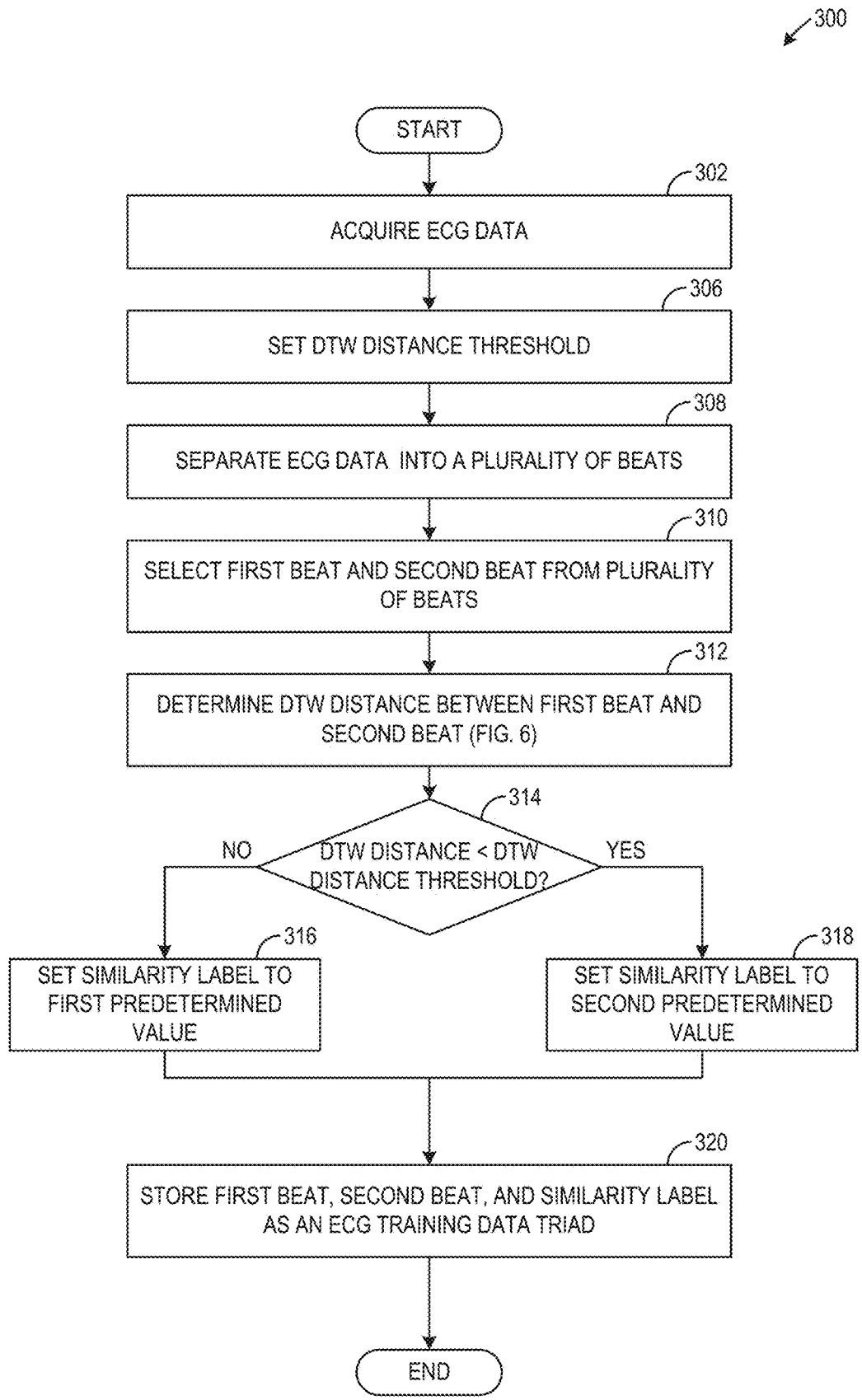
FIG. 3 is a flowchart illustrating a method for generating ECG training data triads, according to an exemplary embodiment of the current disclosure.

Turning to FIG. 3, an example method 300 for automatically generating training data triads is shown. The training data triads generated by method 300 may be used for training a deep neural network in conjunction with training architecture 200. Method 300 may be employed to automatically generate labeled training data (referred to as ECG training data triads, or simply training data triads), bypassing the need for a human expert to manually assess the similarity/dissimilarity of hundreds of thousands of ECG beats. Method 300 thereby enables a substantial decrease in time required to generate a training dataset, as well as enables leveraging of a substantially larger pool of ECG data than would otherwise be available for training. Further, by setting the similarity label of the pair of ECG beats using a DTW distance threshold, wherein DTW distance is phase shift and noise insensitive, the similarity labels may more closely track human intuition of similarity, without requiring use of a human expert to manually label the data. The training data triads generated by method 300 may be used to train a deep neural network, according to one or more of the steps of method 400, to learn a phase shift and noise insensitive mapping from an ECG beat data space, to a feature space. Method 300 may be implemented by one or more of the systems described above. In one embodiment, method 300 may be executed by ECG processing device 120 to generate one or more training data triads.

Method 300 begins at operation 302, wherein the ECG processing device acquires ECG data. In one embodiment, a Holter monitor, such as Holter monitor 102 described above in the description of FIG. 1, may be employed to acquire Holter monitor data from a patient, and the Holter monitor data so obtained may be transferred from the Holter monitor 102 to an ECG processing device, such as ECG processing device 120. In some embodiments, operation 302 may comprise the ECG processing device acquiring previously obtained Holter monitor data from one or more data sources communicably coupled with the ECG processing device. The Holter monitor data may comprise a plurality of beats, collected from one or more patients. In some embodiments, in training a deep neural network to distinguish between beats of a particular demographic, Holter monitor data from patients belonging to said demographic may be selectively acquired at operation 302.

At operation 306, the ECG processing device sets a DTW distance threshold. In one embodiment, operation 306 includes the ECG processing device receiving input from a user, via a user input device, and setting the DTW distance threshold based on the input.

In some embodiments, the ECG processing device comprises machine executable instructions for automatically setting the DTW distance threshold based on one or more preferences selected by a user and/or one or more training protocols for which the training data triads of method 300 are to be used. A larger DTW distance threshold corresponds to a lower barrier for two beats to be considered "similar." Thus, deep neural networks trained using training data triads produced with a larger DTW distance threshold may have less specificity (less ability to distinguish between beats of different classes) but more generalizability and greater insensitivity to noise and phase shift differences between beats. Thus a tradeoff exists between specificity and generalizability as regards setting the DTW distance threshold. In some embodiments, the ECG processing device may automatically set a DTW distance threshold based on a training protocol/method for which the training data triads of method 300 are to be used. In one embodiment, for training a deep neural network to distinguish between beats of a single patient, such as in clustering the beats of a single Holter monitor recording, a smaller DTW distance threshold may be set. In one embodiment, for training a deep neural network to distinguish between beats of a given population/demographic, such as in clustering Holter monitor data of a plurality of patients belonging to a same population/demographic, a larger DTW distance threshold may be set.

In another embodiment, for training deep neural networks to distinguish between beats of mixed populations/demographics, an even larger DTW distance threshold may be set. Thus, the ECG processing device may select a DTW distance threshold such that as the heterogeneity of the use case of a deep neural network increases (e.g., as the heterogeneity of the beats, demographics, etc. for which a deep neural network is to be deployed in determining beat similarity for increases) the DTW distance threshold may correspondingly increase. In one embodiment, a DTW distance threshold is determined based on visual inspection, where a user may visually evaluate pairs of ECG beats, and may select a DTW distance threshold based on the average DTW distance threshold of visually similar beats. In some embodiments, a DTW distance threshold may be selected based on an average intraclass DTW distance within one or more selected classes. A selected DTW distance threshold may be fine-tuned during implementation by adjusting the DTW distance threshold to provide maximal accuracy in classification.

At operation 308, the ECG processing device separates the ECG data received into a plurality of distinct beats. In some embodiments, ECG data may comprise Holter monitor data, wherein the Holter monitor data may comprise a substantially continuous series of beat data, and at operation 308 the ECG processing device may employ one or more algorithms for automatically detecting individual beats within the Holter monitor data, and separating the individual beats into a plurality of separate time series. Beat segmentation may be achieved by implementing one or more beat segmentation algorithms known in the art.

At operation 310, the ECG processing device selects a first beat and a second beat from the plurality of distinct beats. In some embodiments, the ECG processing device may randomly select a first beat and a second beat from the plurality of beats by generating one or more random numbers, using a random number generator, and selecting the first beat and the second beat based on the value of the one or more random numbers. In some embodiments, the first beat and the second beat may be selected intelligently by the ECG processing device based on one or more features of the ECG beats. In one embodiment, the ECG processing device may select ECG beats based on timestamp, heart rate, time of day, or other metadata data features of the ECG beats.

At operation 312, the ECG processing device determines a DTW distance between the first beat and the second beat. Briefly, DTW is an algorithm that calculates a minimum distance between two given sequences (e.g., between pairs of ECG beat data, comprising two distinct time series of voltage measurements) with certain rules. The rules include: every time point from the first beat must be matched with one or more time points from the second beat, and vice versa; the first time point from the first beat must be matched with the first time point from the second beat (but it does not have to be its only match); the last time point from the first beat must be matched with the last time point from the second beat (but it does not have to be its only match); and the mapping of the time points from the first beat to the time points of the second beat must be monotonically increasing, and vice versa. The minimum distance (simply referred to herein as the DTW distance) is the smallest DTW distance which satisfies the above restrictions, where the distance is computed as the sum of absolute differences for each voltage measurement of each matched pair of time points between the first beat and the second beat. The minimum distance between the two time series is determined by non-linear warping of the time dimension, essentially contracting or expanding portions of the time series data, while following the above described rules, until a minimum distance is obtained. The distance determined thereby is the DTW distance between the first beat and the second beat.

Figure 6:
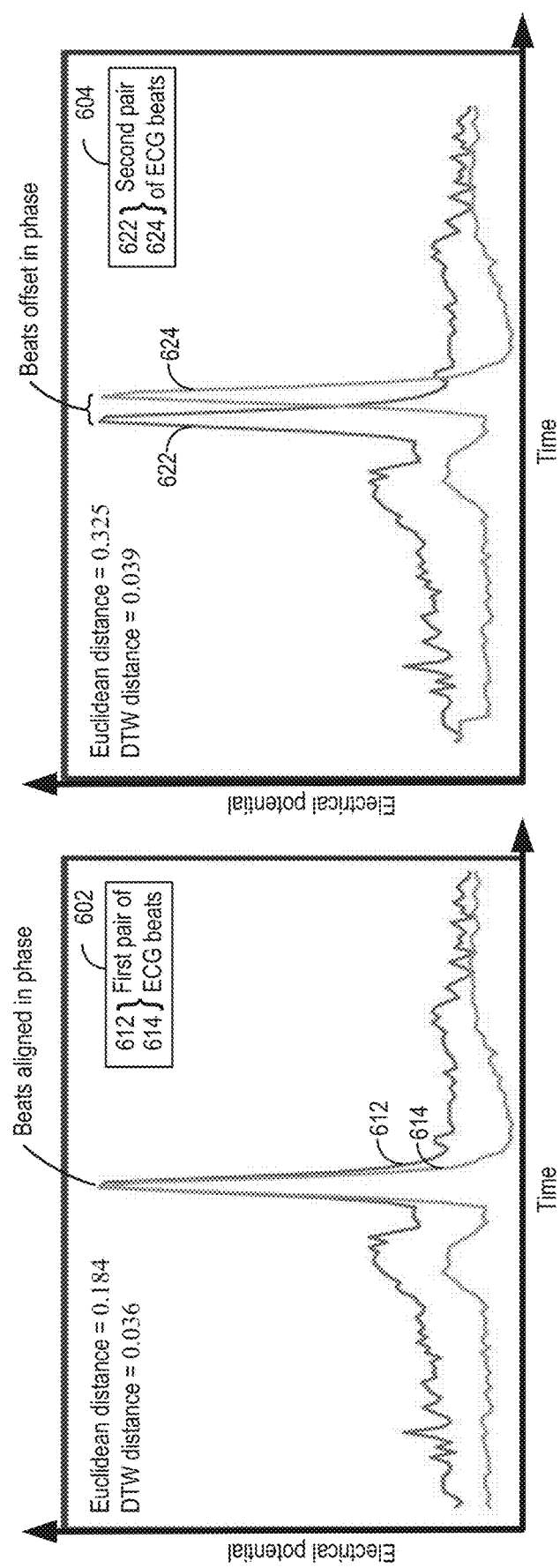
FIG. 6 shows an example of a pair of phase shifted beats, and an example of a pair of in-phase ECG beats

FIG. 6 illustrates the difference between a DTW distance and a conventional similarity metric. Turning briefly to FIG. 6, a first pair of ECG beats 602 and a second pair of ECG beats 604 are shown. The first pair of ECG beats 602 comprises a first curve 612 corresponding to a first ECG beat and a second curve 614 corresponding to a second ECG beat. The first curve 612 and the second curve 614 are aligned in phase, in the first pair of ECG beats 602. The second pair of ECG beats 604 comprises a first curve 622 corresponding to a first ECG beat and a second curve 624 corresponding to a second ECG beat. The first curve 622 and the second curve 624 are misaligned in phase, that is, there is a phase offset between the second pair of ECG beats 604. Conventional similarity metrics, such as Euclidean distance, may label first pair of ECG beats 602 as "similar" and second pair of ECG beats 604 as "dissimilar," despite the fact that the first and second pairs of beats are identical, apart from a phase shift/offset. In contrast, a DTW distance determined for the first pair of beats 602 may be substantially similar to a DTW distance determined for the second pair of beats 604. In particular, for the first pair of ECG beats 602, the Euclidian distance is 0.184, while the DTW distance is 0.036, and for the second pair of ECG beats 604, the Euclidean distance is 0.325 while the DTW distance is 0.039. Thus it can be seen that the Euclidean distance is strongly dependent on the phase shift between the two beats, whereas the DTW distance is relatively phase shift invariant.

At operation 314, the ECG processing device compares the DTW distance determined at operation 312 against the DTW distance threshold set at operation 306. If at operation 314, the ECG processing device determines that the DTW distance between the first beat and the second beat is equal to or greater than the DTW distance threshold, method 300 may proceed to operation 316.

At operation 316, the ECG processing device sets a similarity label for the first beat and the second beat to a first predetermined value, wherein the first predetermined value indicates that the first beat and the second beat are dissimilar. In one embodiment, the similarity label may comprise a binary label, wherein a label having a value of 0 indicates the DTW distance between the first beat and the second beat is within the DTW distance threshold, and wherein a non-zero value (e.g., 1, −1, etc.) may indicate that the DTW distance between the first ECG beat and the second ECG beat is not within the DTW distance threshold. Following operation 316, method 300 may proceed to operation 320.

However, if at operation 314, the ECG processing device determines that the DTW distance between the first beat and the second beat is less than the DTW distance threshold, method 300 proceeds to operation 318, wherein the ECG processing device sets a similarity label for the first beat and the second beat (herein also referred to as a beat pair), to a second predetermined value, indicating that the first beat and the second beat are "similar." Method 300 may then proceed to operation 320.

At operation 320, the ECG processing device stores the first beat, the second beat, and the similarity label, in a pre-determined location of non-transitory memory, as an ECG training data triad. In some embodiments, the ECG processing device may store the training data triad (comprising the first beat, the second beat, and the similarity label) in an ECG data module, such as ECG data module 134. In some embodiments, the training data triad may be added to a training dataset, comprising a plurality of training data triads. In some embodiments, at operation 320, the ECG processing device may receive input from a user input device accepting or rejecting the similarity label, and responding to receiving input from the user input device rejecting the similarity label by switching the similarity label from a first predetermined value to a second predetermined value. This provides a mechanism whereby a deep neural network may be "fined tuned" during implementation by enabling a clinician or other user to re-label a portion of the automatically generated training data.

It will be appreciated that method 300 may be repeated to produce a plurality of training data triads. In some embodiments, method 300 may be repeated a pre-determined number of times, to produce a training dataset comprising the pre-determined number of training data triads.

Thus, method 300 enables automatic generation of training data triads, for training a deep neural network, such as a siamese neural network, to learn a phase shift and noise insensitive mapping from an ECG data space to feature space. A recognized challenge in the field of machine learning is the difficulty of obtaining labeled training datasets of sufficient size and variety to enable training of a robust model. Method 300 at least partially addresses this issue by determining similarity labels using a DTW distance threshold, thereby bypassing the need for manual similarity label determination by a human expert.

A technical effect of determining a similarity label using a DTW distance threshold is that a training dataset may be more rapidly produced, with minimal or no human intervention, and enabling a similarity label to more closely correlate with human expert determined similarity, as DTW distance is insensitive to phase shift and time warping noise.

Turning to FIG. 4, an example of a training method 400, which may be executed by one or more of the systems described above, is shown. In one embodiment, method 400 may be used in conjunction with training architecture 200 to train first subnetwork 201a and second subnetwork 201b, to map ECG beat data to feature space embeddings, using automatically generated training data triads, such as the training data triads discussed in method 300, above.

Method 400 begins at operation 402, where the ECG processing device selects a training data triad comprising a first beat, a second beat, and a similarity label. The training data triad may comprise a training data triad generated according to one or more of the operations of method 300, discussed in more detail above. In some embodiments, a training data triad may be selected from a repository of training data, such as may be stored in ECG data module 134 of ECG processing device 120, based on metadata associated therewith. In some embodiments, training data triads may be selected for training a siamese neural network to distinguish ECG beats within a particular demographic, population, or in a particular use case, and in such instances the ECG training data triad may be selected based on one or more pieces of metadata pertaining thereto, indicating the demographic/population/use-case from which the training data triad was derived, matches the demographic/population/use-case for which the siamese neural network is to be trained.

At operation 404, the ECG processing device maps the first beat to a first feature space embedding using the siamese neural network. Operation 404 may include inputting the first ECG beat into a first subnetwork of the siamese neural network, and projecting the ECG beat data to a feature space embedding, comprising an n-dimensional vector characterizing the features of the ECG beat, by passing the ECG beat data of the first ECG beat through a plurality of layers of the first subnetwork.

At operation 406, the ECG processing device maps the second beat to a second feature space embedding using the siamese neural network. Operation 404 may include inputting the second ECG beat into a second subnetwork of the siamese neural network, and projecting the ECG beat data to a feature space embedding, comprising an n-dimensional vector characterizing the features of the ECG beat, by passing the ECG beat data of the second ECG beat through a plurality of layers of the second subnetwork.

At operation 408, the ECG processing device calculates a loss using the first feature space embedding, the second feature space embedding, and the similarity label, using a loss function. In some embodiments, operation 408 may comprise the ECG processing device determining a contrastive loss using contrastive loss function 230, discussed above with reference to FIG. 2. In one embodiment, the loss function may comprise a contrastive loss L, wherein the loss is calculated as a function of the similarity label, and the proximity of the first and second feature space embedding, according to the below equation:

$$L(F(x_i), F(x_j), Y) = (1-Y) \cdot \frac{1}{2} \cdot (D_w)^2 + (Y) \cdot \frac{1}{2} \cdot \max(0, m - D_w)^2$$

where L( ) is the contrastive loss function, $F(x_i)$ is the first feature space embedding corresponding to the first beat $x_i$, $F(x_j)$ is the second feature space embedding corresponding to the second beat $x_j$, $D_w$ is a distance (e.g., the Euclidean distance in the feature space) between the first and second feature space embeddings, m is a pre-determined margin, and Y is the similarity label, wherein Y is set to one (1) when the first beat and second beat are not similar, and wherein Y is set to zero (0) when the first beat and the second beat are similar.

It will be appreciated that the current disclosure encompasses use of loss functions other than the contrastive loss function given above. In particular, the current disclosure encompasses variations of the above loss function, such as multiplying one or more terms by a constant, or adding a constant to one or more terms of the above equation, and other variations. In some embodiments, a triplet loss function may be used at operation 408, and in such embodiments, the ECG processing device may generate a training data triplet, comprising a first beat of a first class, a second beat of the first class, and a third beat not of the first class, wherein the first beat may be randomly selected, and wherein the DTW distance threshold may be used to select the second beat and third beat, based on the second beat being less than the threshold DTW distance from the first beat, and based on the third beat being equal to or greater than the DTW distance away from the first beat, respectively.

At operation 410, ECG processing device adjusts parameters of the siamese neural network by backpropagating the loss through the layers of the first and second subnetworks of the siamese neural network using a backpropagation algorithm. In one embodiment, operation 410 comprises the ECG processing device adjusting the weights and biases of the layers of the first and second subnetwork based on the loss calculated at operation 408. In some embodiments, back propagation of the loss may comprise employing a gradient descent algorithm, wherein a gradient of the loss function (a first derivative, or approximation of the first derivative) is determined for each weight and bias of the siamese neural network. Each weight (and bias) of the siamese neural network is then updated by adding the negative of the product of the gradient determined (or approximated) for the weight (or bias) and a predetermined step size, according to the below equation:

$$P_{i+1} = P_i - \eta \frac{\partial \text{Error}}{\partial P_i}$$

where $P_{i+1}$ is the updated parameter value, $P_i$ is the previous parameter value, $\eta$ is the step size, and $$\frac{\partial \text{Error}}{\partial P_i}$$

is the partial derivative of the error with respect to the previous parameter.

Following operation 410, method 400 may end. It will be appreciated that method 400 may be repeated until one or more pre-determined conditions are met. In some embodiments, the one or more pre-determined conditions may include convergence of the weights and biases of the siamese neural network (that is, a rate of change of the parameters of the siamese neural networks decreases to below a pre-determined threshold rate), the loss determined at operation 408 decreasing to below a pre-determined, non-zero, threshold, etc. In some embodiments, the loss may be determined using a validation dataset, wherein the validation dataset is distinct from the training dataset, and comprises ECG beats not seen by the model during training. In this way, method 400 enables a deep neural network to learn a phase shift and noise insensitive mapping from an ECG data domain to a feature domain, wherein beats comprising similar topology, may be mapped to proximate points in feature space, and wherein topologically dissimilar beats may be mapped to regions in the feature space separated by greater than a pre-determined margin distance (m).

Figure 5:
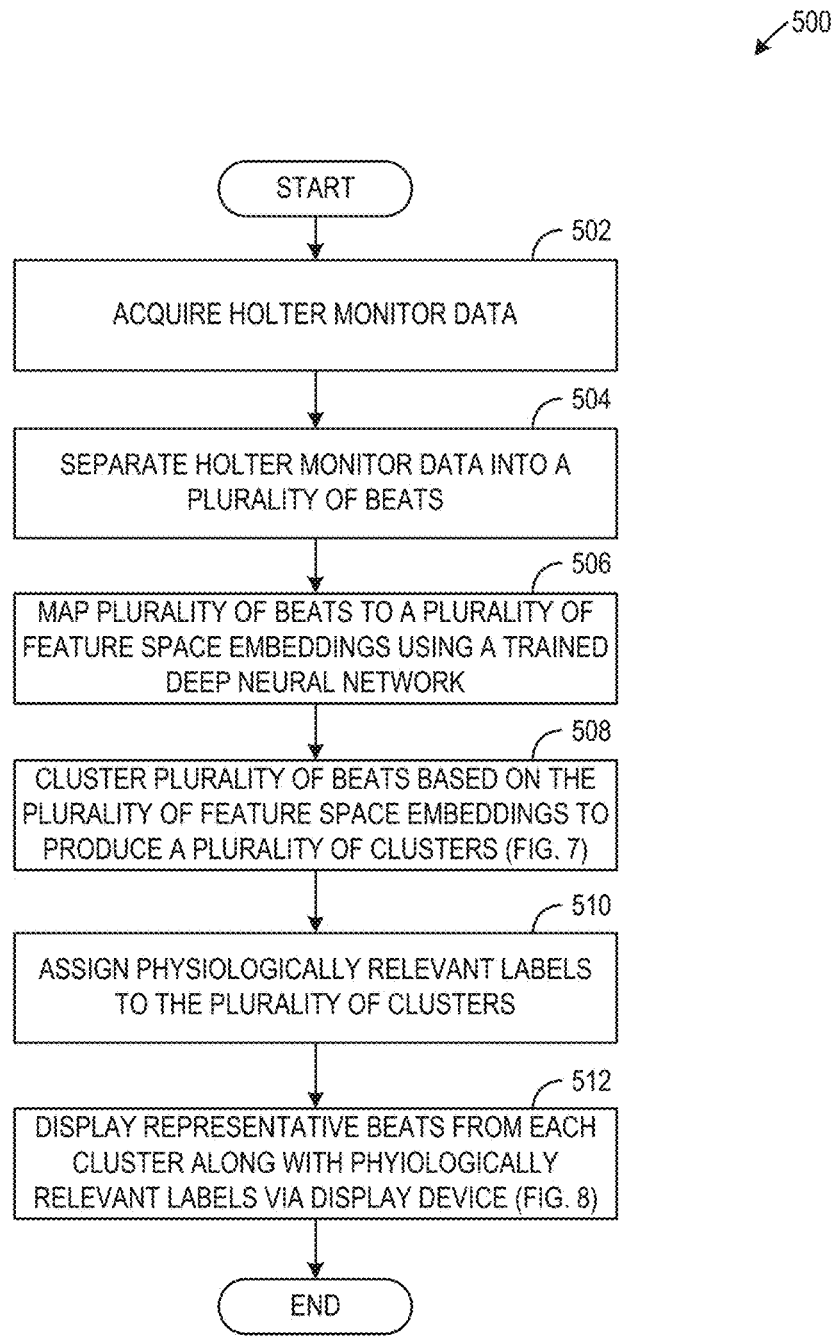
FIG. 5 shows a flowchart illustrating a method for implementing a trained deep neural to map ECG data for a plurality of beats to a plurality of feature space embeddings, and to cluster the plurality of beats based on the plurality of feature space embeddings, according to an exemplary embodiment of the current disclosure.

Turning to FIG. 5, an example method 500 for automatically clustering the ECG data of a Holter monitor recording using a trained deep neural network is shown. Method 500 may be executed by one or more of the systems described herein, based on machine executable instructions stored in non-transitory memory, wherein the non-transitory memory further stores a trained deep neural network, which may have been trained using training architecture 200, in conjunction with method 400, discussed above.

Method 500 begins at operation 502, where a Holter monitor is used to acquire Holter monitor data. In some embodiments, operation 502 may comprise a patient wearing a Holter monitor, such as Holter monitor 102, for a prescribed duration of time. In one embodiment, the prescribed duration of time may comprise 24 hours to 48 hours, and any fractional portion of time therebetween. During the prescribed duration of time, the Holter monitor may continuously, or semi-continuously monitor the electrical activity of a patient's heart using two or more electrodes configured to measure two or more leads. The electrical activity so recorded may be stored as a time series of electrical potential difference (voltage), in one or more formats known in the art of Holter monitoring. In some embodiments, the Holter monitor may sample and record the voltage signal at regular intervals of time (e.g., every 5 kHz to every 50 Hz, and any fractional portion thereof). The Holter monitor may be communicably coupled with an ECG processing device, such as ECG processing device 120, and may transfer a Holter monitor recording of a patient to ECG processing device 120.

At operation 504, the ECG processing device separates the Holter monitor data into a plurality of beats. In one embodiment, the ECG data processing device separates the Holter monitor data into a plurality of beats using a processor to execute machine readable instructions that when executed cause the processor to evaluate the Holter monitor data for pre-determined, repeating patterns, wherein a single cycle of the pattern is designated as a beat, and each beat is separated as a distinct time series. In some embodiments, the ECG processing device may employ one or more algorithms known in the art of electrocardiography for automatically detecting individual beats within the Holter monitor data, and separating the individual beats into a plurality of separate time series. Each of the plurality of beats so produced may be indexed according to one or more pieces of metadata. In some embodiments, the metadata may include a timestamp (indicating a time of acquisition of the ECG beat), a heart rate, a time of day, etc.

At operation 506, the ECG processing device maps the plurality of beats to a plurality of feature space embeddings using the trained deep neural network. In one embodiment, the ECG processing device may select a siamese neural network, trained according to one or more steps of method 400 using training data triads produced via method 300. The ECG processing device may select the siamese neural network based on a population/demographic/use-case for which the siamese neural network was trained, wherein the population/demographic/use-case for which a siamese neural network was trained may be indicated by one or more pieces of metadata associated with the siamese neural network. The selected siamese neural network may receive each of the plurality of beats, and may map each of the beats to a corresponding feature space embedding by passing the ECG beat data of the plurality of beats through a plurality of layers of the siamese neural network, to produce a plurality of feature space embeddings. In some embodiments, a subnetwork of the siamese neural network may be used to map the plurality of ECG beats, in series, to a corresponding plurality of feature space embeddings. In another embodiment, a plurality of subnetworks may map the plurality of ECG beats, in parallel, to a plurality of feature space embeddings. The plurality of feature space embeddings comprise an encoding of the latent features within the plurality of beats. Similar beats, invariant of phase shift and noise, may be mapped to a particular region, such that distinct classes of beats are mapped to distinct regions of the feature space.

At operation 508, the ECG processing device clusters the plurality of beats, based on the plurality of feature space embeddings, to produce a plurality of clusters. In some embodiments, the ECG processing device includes machine executable instructions, that when executed by the processor, perform one or more steps of a clustering algorithm, such as a k-means clustering algorithm. Turning briefly to FIG. 7, a two-dimensional projection 702 of the plurality of feature space embeddings, corresponding to a plurality of ECG beats of a Holter monitor recording, is shown. As can be seen, beats of different classes are resolved into distinct clusters (shown in outline) of high purity, wherein purity is a measure of how "alike" all beats within a cluster are, measured as the ratio of the number of beats belonging to the most prevalent class within a cluster, to the total number of beats within the cluster. FIG. 7 shows clear separation between clusters, and high purity of clusters, indicating a siamese neural network, trained according to one or more of the steps of method 400, using training data triads produced according to one or more of the steps of method 300, is able to learn a robust mapping from an ECG data space to a feature space, insensitive to phase shifts and noise. In FIG. 7, a region 704 is outlined by a solid line. A region 710 is outlined by a dashed line. A region 706 is outlined by a long-dashed line. A region 714 is outlined by a short-dashed line. A region 716 is outlined by a closely-spaced dotted line. A region 718 is outlined by a farther-spaced dotted line. A region 708 is outlined by a dash-dotted line. A region 712 is outlined by a double-dotted dashed line.

At operation 510, the ECG processing device assigns physiologically relevant labels to the plurality of clusters. In some embodiments, a label for each cluster is determined based on a most prevalent class within the cluster. In some embodiments, the morphology of ECG beats is used to determine the physiologically relevant label. In some embodiments, annotations provided by expert cardiologists may be used for determining the physiologically relevant labels of the clusters.

At operation 512, the ECG processing device displays representative beats from each cluster along with a corresponding physiological label via a display device. In some embodiments, a beat may be selected from each distinct cluster, to provide a compressed/template view of the data within a Holter monitor recording.

Figure 8:
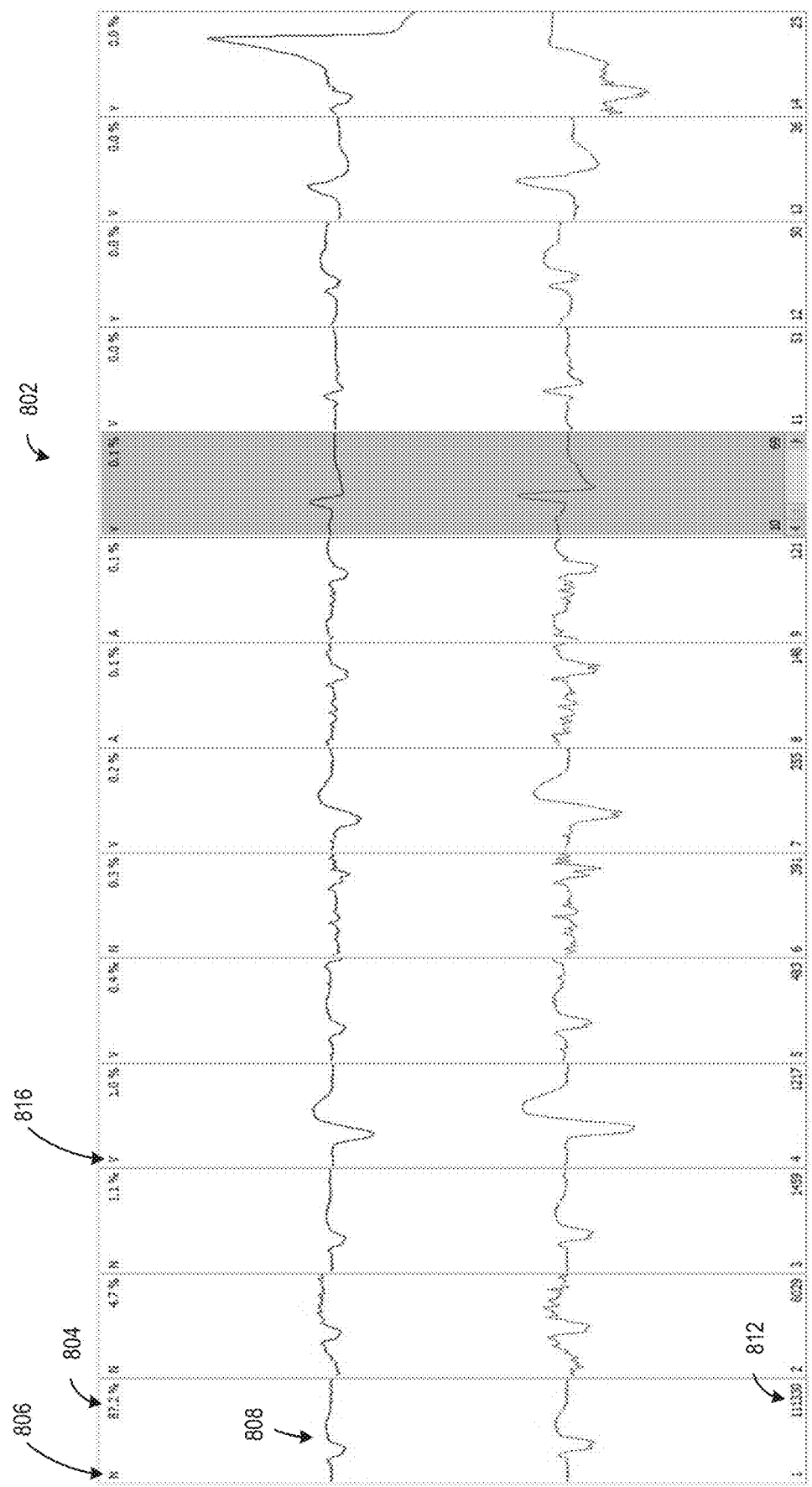
FIG. 8 shows an example of a template view of ECG beats, which may be produced using clustered ECG data produced according to exemplary embodiments of the current disclosure.

Turning briefly to FIG. 8, one example of a template view 802, which may be displayed at operation 512 is shown. Template view 802 shows representative beats from each distinct cluster identified at operation 508. Each representative beat, such as representative beat 808, includes an indication of the total number of beats from the same cluster as the representative beat (e.g., number of similar beats 812), a relative abundance of the cluster of beats represented by the representative beat (e.g., relative abundance 804), and a physiological label of the cluster of beats represented by the representative beat (e.g., physiological label 806).

Each distinct column shown in template view 802 corresponds to a distinct cluster of beats. One or more beats from each cluster may be shown within each column to represent the overall appearance/characteristics of the beats within the corresponding cluster. As an example, the leftmost column of template view 802 includes first representative beat 808, which provides an example of the shape characteristics of the beats within the cluster corresponding to the leftmost column. Each column may further include a physiological label, such as physiological label 806. The physiological label may indicate to which of a plurality of pre-defined classes the given cluster belongs. The leftmost column corresponds to a "normal" beat class, as indicated by physiological label 806. Contrastingly, the fourth column from the left includes a second physiological label 816, indicating the cluster of beats corresponds the pre-defined class of beats referred to as ventricular beats.

Each column in template view 802 further indicates the total number of beats within the corresponding cluster. For example, number of similar beats 812, shown in the bottom right-hand corner of the leftmost column, indicates that 111,330 beats belong to the cluster summarized by the leftmost column. Each column further shows the relative abundance of the beats within the corresponding cluster, for example, relative abundance 804 shows that the relative abundance of beats corresponding to the leftmost column is 87.2%. In other words, relative abundance 804 indicates that 87.2% of beats in the beat data under evaluation are grouped into the cluster represented by representative beat 808.

By displaying representative beats from each distinct cluster, redundant beats are not shown, enabling a clinician to view a more compact representation of the data obtained by a Holter monitor. Each representative beat may include a visual indication of the relative abundance of the beats belonging to the cluster, (e.g., cluster 1, 32.1%), further enabling a clinician to rapidly identify rare/irregular beats, and to compare the relative abundance of beats of various physiological classes. Selection of representative beats from a given cluster may comprise determining a center point of the cluster (e.g., an average position of each point in the cluster), in feature space, and selecting a beat whose feature space embedding is closest to the center of the cluster. In some embodiments, an average time series of each beat in a cluster may be calculated, and the average time series may be used as the representative beat for the cluster.

Following operation 512, method 500 may end. In this way, an ECG processing device may automatically cluster a plurality of ECG data obtained during a Holter monitor recording, using a trained deep neural network, wherein the clusters so produced may more closely match a human intuition of beat similarity by mapping beats of similar topology to similar points in the feature space, invariant of phase shift, differences in heart rate, etc. As an example, two identical beats, at two different heart rates, may appear similar to a human expert, but may be misclassified as belonging to distinct clusters using a conventional Holter monitor data clustering technique. However, method 500 enables topologically similar beats, at different heart rates and measured at different phases, to be mapped to substantially similar locations in a feature space, enabling generation of clusters corresponding more closely to human intuition of similarity, and with a high degree of purity.

When introducing elements of various embodiments of the present disclosure, the articles "a," "an," and "the" are intended to mean that there are one or more of the elements. The terms "first," "second," and the like, do not denote any order, quantity, or importance, but rather are used to distinguish one element from another. The terms "comprising," "including," and "having" are intended to be inclusive and mean that there may be additional elements other than the listed elements. As the terms "connected to," "coupled to," etc. are used herein, one object (e.g., a material, element, structure, member, etc.) can be connected to or coupled to another object regardless of whether the one object is directly connected or coupled to the other object or whether there are one or more intervening objects between the one object and the other object. In addition, it should be understood that references to "one embodiment" or "an embodiment" of the present disclosure are not intended to be interpreted as excluding the existence of additional embodiments that also incorporate the recited features.

In addition to any previously indicated modification, numerous other variations and alternative arrangements may be devised by those skilled in the art without departing from the spirit and scope of this description, and appended claims are intended to cover such modifications and arrangements. Thus, while the information has been described above with particularity and detail in connection with what is presently deemed to be the most practical and preferred aspects, it will be apparent to those of ordinary skill in the art that numerous modifications, including, but not limited to, form, function, manner of operation and use may be made without departing from the principles and concepts set forth herein. Also, as used herein, the examples and embodiments, in all respects, are meant to be illustrative only and should not be construed to be limiting in any manner.

The invention claimed is:

1. A method comprising:
   selecting a first beat and a second beat;
   determining a dynamic time warping (DTW) distance between the first beat and the second beat;
   setting a similarity label for the first beat and the second beat based on the DTW distance;
   storing the first beat, the second beat, and the similarity label, in a location of non-transitory memory as an electrocardiogram (ECG) training data triad; and
   training a deep neural network with the ECG training data triad.

2. The method of claim 1, wherein setting the similarity label for the first beat and the second beat based on the DTW distance comprises:
   comparing the DTW distance against a DTW distance threshold; and
   responding to the DTW distance being less than the DTW distance threshold by:
      setting the similarity label to a first predetermined value indicating the first beat and the second beat are similar; or
   responding to the DTW distance being greater than the DTW distance threshold by:
      setting the similarity label to a second predetermined value indicating the first beat and the second beat are dissimilar.

3. The method of claim 2, wherein the DTW distance threshold is set based upon input from a user input device, wherein one or more of the first and second beats is recorded via one or more Holter monitors, and wherein training the deep neural network comprises training the deep neural network to map beats separated by less than the threshold DTW distance to similar points in a feature space, and to map beats separated by greater than the threshold DTW distance to points in the feature space separated by greater than a pre-determined Euclidean distance.

4. The method of claim 2, wherein training the deep neural network with the ECG training data triad comprises:
   feeding the ECG training data triad to the deep neural network;
   mapping the first beat to a first feature space embedding using the deep neural network;
   mapping the second beat to a second feature space embedding using the deep neural network;
   calculating a loss using the first feature space embedding, the second feature space embedding, and the similarity label; and
   adjusting weights and biases of the deep neural network based on the loss.

5. The method of claim 4, wherein the deep neural network is a siamese neural network.

6. The method of claim 4, wherein calculating the loss using the first feature space embedding, the second feature space embedding, and the similarity label comprises determining a contrastive loss between the first feature space embedding and the second feature space embedding based on the similarity label.

7. The method of claim 4, wherein adjusting weights and biases of the deep neural network based on the loss comprises backpropagating the loss through the deep neural network and adjusting the weights and biases of the deep neural network using a gradient descent algorithm.

8. The method of claim 1, the method further comprising:
   upon training the deep neural network with the ECG training data triad to produce a trained deep neural network:
      receiving Holter monitor data;
      separating the Holter monitor data into a plurality of beats;
      mapping the plurality of beats to a plurality of feature space embeddings using the trained deep neural network and without performing calculations of DTW distances between any of the plurality of beats;
      clustering the plurality of beats based on the plurality of feature space embeddings to produce a plurality of clusters;
      assigning physiologically relevant labels to the plurality of clusters; and
      displaying representative beats from each of the plurality of clusters along with the physiologically relevant labels via a display device.

9. The method of claim 8, wherein the Holter monitor data comprises three channel ECG data, and wherein the three channel ECG data comprises over one hundred thousand beats.

10. The method of claim 8, wherein clustering the plurality of beats based on the plurality of feature space embeddings to produce a plurality of clusters comprises clustering the plurality of feature space embeddings using a k-means clustering algorithm on the plurality of feature space embeddings.

11. A method comprising:
   selecting a first beat and a second beat from a plurality of beats;
   determining a dynamic time warping (DTW) distance between the first beat and the second beat;
   setting a similarity label for the first beat and the second beat based on the DTW distance;
   mapping the first beat to a first feature space embedding using the deep neural network;
   mapping the second beat to a second feature space embedding using the deep neural network;
   calculating a loss using the first feature space embedding, the second feature space embedding, and the similarity label; and
   adjusting weights and biases of the deep neural network based on the loss.

12. The method of claim 11, wherein selecting the first beat and the second beat from the plurality of beats comprises randomly selecting the first beat and the second beat from the plurality of beats.

13. The method of claim 11, wherein the first beat and the second beat comprise ECG data recorded by a Holter monitor.

14. The method of claim 11, the method further comprising:

receiving input from a user input device accepting or rejecting the similarity label; and responding to receiving input from the user input device rejecting the similarity label by:

switching the similarity label from a first predetermined value to a second predetermined value.

15. The method of claim 11, wherein setting the similarity label for the first beat and the second beat based on the DTW distance comprises:

comparing the DTW distance against a DTW distance threshold; and responding to the DTW distance being less than the DTW distance threshold by:

setting the similarity label to a first predetermined value indicating the first beat and the second beat are similar; or responding to the DTW distance being greater than the DTW distance threshold by:

setting the similarity label to a second predetermined value indicating the first beat and the second beat are dissimilar.

16. An electrocardiogram (ECG) processing device comprising:

a display device;

a user input device;

a memory storing a deep neural network and instructions; and a processor communicably coupled to the display device, the user input device, and the memory, and when executing the instructions, configured to:

select a first beat and a second beat from a plurality of ECG beat data;

determine a dynamic time warping (DTW) distance between the first beat and the second beat;

set a similarity label for the first beat and the second beat based on the DTW distance and a DTW distance threshold, wherein the DTW distance threshold is set based on user input received from the user input device;

train the deep neural network using at least the first beat, the second beat, and the similarity label, to produce a trained deep neural network;

receive Holter monitor data;

separate the Holter monitor data into a plurality of beats;

map the plurality of beats to a plurality of feature space embeddings using the trained deep neural network;

cluster the plurality of beats based on the plurality of feature space embeddings to produce a plurality of clusters;

assign physiological labels to the plurality of clusters; and display a plurality of representative beats corresponding to the plurality of clusters, along with corresponding physiological labels via the display device.

17. The ECG processing device of claim 16, wherein the processor is configured to cluster the plurality of beats based on the plurality of feature space embeddings to produce the plurality of clusters by clustering the plurality of feature space embeddings using a k-means clustering algorithm.

18. The ECG processing device of claim 17, wherein a representative beat of the plurality of representative beats is selected based on a Euclidean distance in feature space between the representative beat and a center of an associated cluster.

19. The ECG processing device of claim 17, wherein the plurality of clusters consists of k clusters, and wherein k is set based on input received via the user input device.

20. The ECG processing device of claim 16, wherein, when executing the instructions, the processor is further configured to:

receive a particular beat;

map the particular beat to a particular feature space embedding; and group the particular beat into a cluster of the plurality of clusters based on a Euclidean distance between a center of the cluster and the particular feature space embedding.

* * * * *